(12) United States Patent
Haefner

(10) Patent No.: US 8,406,881 B2
(45) Date of Patent: Mar. 26, 2013

(54) VARIABLE VOLTAGE COMPLIANCE FOR CURRENT OUTPUT GENERATOR

(75) Inventor: Paul A. Haefner, Circle Pines, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/220,215

(22) Filed: Aug. 29, 2011

(65) Prior Publication Data

US 2011/0313492 A1 Dec. 22, 2011

Related U.S. Application Data

(63) Continuation of application No. 11/457,385, filed on Jul. 13, 2006, now Pat. No. 8,014,866.

(51) Int. Cl.
*A61N 1/08* (2006.01)

(52) U.S. Cl. .................. 607/28; 607/7; 607/8; 607/62; 607/115; 607/116

(58) Field of Classification Search .................. 607/2–8, 607/25, 115, 116, 62
See application file for complete search history.

(56) References Cited

U.S. PATENT DOCUMENTS

| | | | |
|---|---|---|---|
| 5,243,975 | A | 9/1993 | Alferness |
| 6,516,227 | B1 | 2/2003 | Meadows et al. |
| 6,970,741 | B1 * | 11/2005 | Whitehurst et al. ............ 607/3 |
| 2003/0074032 | A1 | 4/2003 | Gliner |
| 2003/0135248 | A1 | 7/2003 | Stypulkowski |
| 2003/0144710 | A1 | 7/2003 | Haugland et al. |
| 2003/0153959 | A1 | 8/2003 | Thacker |
| 2003/0236558 | A1 * | 12/2003 | Whitehurst et al. ............ 607/45 |
| 2004/0116978 | A1 * | 6/2004 | Bradley ............ 607/48 |
| 2004/0186517 | A1 | 9/2004 | Hill |
| 2005/0070971 | A1 | 3/2005 | Fowler et al. |
| 2006/0229688 | A1 * | 10/2006 | McClure et al. ............ 607/72 |
| 2007/0135868 | A1 * | 6/2007 | Shi et al. ............ 607/62 |
| 2008/0015657 | A1 | 1/2008 | Haefner |

OTHER PUBLICATIONS

"U.S. Appl. No. 11/457,385, Advisory Action mailed Oct. 1, 2009", 3 pgs.
"U.S. Appl. No. 11/457,385, Advisory Action mailed Oct. 18, 2010", 3 pgs.
"U.S. Appl. No. 11/457,385, Examiner Interview Summary mailed May 3, 2011", 2 pgs.
"U.S. Appl. No. 11/457,385, Final Office Action mailed Jun. 23, 2010", 13 pgs.
"U.S. Appl. No. 11/457,385, Final Office Action mailed Jul. 16, 2009", 13 pgs.
"U.S. Appl. No. 11/457,385, Non-Final Office Action mailed Dec. 22, 2009.", 13 Pgs.
"U.S. Appl. No. 11/457,385, Non-Final Office Action mailed Dec. 23, 2008", 12 pgs.

(Continued)

*Primary Examiner* — Niketa Patel
*Assistant Examiner* — Hiba El-Kaissi
(74) *Attorney, Agent, or Firm* — Schwegman Lundberg & Woesnner, P.A.

(57) ABSTRACT

A system for providing stimulation current in implantable medical devices is provided. One aspect of this disclosure relates to an apparatus including a power supply terminal adapted to be connected to a power supply. The apparatus embodiment also includes circuitry connected to the power supply terminal and adapted to detect a parameter dependent on tissue/electrode impedance. The apparatus embodiment further includes a current output pulse generator adapted to deliver electrical therapy. The current generator includes an adjustable compliance voltage source connected to the power supply terminal. The compliance voltage source has a programmable amplitude and is adapted to provide different potentials for different tissue/electrode interface impedances. According to various embodiments, the apparatus embodiment also includes at least one stimulating electrode, and the current generator is adapted to deliver electrical therapy using the electrode. Other aspects and embodiments are provided herein.

18 Claims, 5 Drawing Sheets

OTHER PUBLICATIONS

"U.S. Appl. No. 11/457,385, Notice of Allowance mailed May 3, 2011", 21 pgs.

"U.S. Appl. No. 11/457,385, Reference filed Sep. 22, 2010 to Final Office Action mailed Jun. 23, 2010", 14 pgs.

"U.S. Appl. No. 11/457,385, Response filed Mar. 23, 2009 to Non Final Office Action mailed Dec. 23, 2008", 13 pgs.

"U.S. Appl. No. 11/457,385, Response filed Sep. 15, 2009 to Final Office Action mailed Jul. 16, 2009", 13 pgs.

"U.S. Appl. No. 11/457,385, Response filed Oct. 16, 2009 to Advisory Action mailed Jul. 16, 2009", 13 pgs.

"U.S. Appl. No. 11/457,385, Response filed Nov. 23, 2010 to Final Office Action mailed Jun. 23, 2010", 16 pgs.

"U.S. Appl. No. 11/457,385, Response filed Mar. 22, 2010 to Non Final Office Action mailed Dec. 22, 2009", 14 pgs.

"U.S. Appl. No. 11/457,385, Supplemental Notice of Allowance mailed Aug. 8, 2011", 18 pgs.

* cited by examiner

VARIABLE VOLTAGE COMPLIANCE FOR CURRENT OUTPUT GENERATOR

CLAIM OF PRIORITY

This application is a continuation of and claims the benefit of priority under 35 U.S.C. §120 to U.S. patent application Ser. No. 11/457,385, filed on Jul. 13, 2006, now issued as U.S. Pat. No. 8,014,866, which is hereby incorporated by reference herein in its entirety.

TECHNICAL FIELD

This disclosure relates generally to implantable medical devices and, more particularly, to systems for providing stimulation current.

BACKGROUND

Current output devices, as compared to voltage output devices, may provide superior neural recruitment characteristics during neural stimulation from an implantable medical device (IMD). However, the current output device requires a compliance voltage sufficient to drive stimulation current through a tissue/electrode interface. Because of variation in tissue/electrode interface impedance, the compliance voltage requirements can negatively impact battery longevity. Thus, there is a need for improved systems for providing stimulation current in implantable medical devices.

SUMMARY

Disclosed herein, among other things, is system for providing stimulation current from an implantable medical device. One aspect of this disclosure relates to an apparatus including a power supply terminal adapted to be connected to a power supply. The apparatus embodiment also includes circuitry connected to the power supply terminal and adapted to detect a parameter dependent on tissue/electrode impedance. The apparatus embodiment further includes a current output pulse generator adapted to deliver electrical therapy. The current generator includes an adjustable compliance voltage source connected to the power supply terminal. The compliance voltage source has a programmable amplitude and is adapted to provide different potentials for different tissue/electrode interface impedances.

An apparatus embodiment includes a power supply and circuitry adapted to detect tissue/electrode impedance and further adapted to be connected to the power supply. The apparatus embodiment also includes a current output pulse generator adapted to deliver electrical therapy. The current generator includes an adjustable compliance voltage source connected to the power supply. The compliance voltage source has a programmable amplitude and is adapted to provide different potentials for different tissue/electrode interface impedances. According to various embodiments, the apparatus embodiment also includes at least one stimulating electrode, and the current output pulse generator is adapted to deliver electrical therapy using the electrode.

One aspect of this disclosure relates to a method for making a system for providing stimulation current from an implantable medical device. An embodiment of the method includes forming circuitry adapted to detect a parameter dependent on tissue/electrode impedance. The method embodiment also includes forming a current output pulse generator adapted to deliver electrical therapy, the generator including a compliance voltage source having a programmable amplitude and adapted to provide different potentials for different tissue/electrode interface impedances.

One aspect of this disclosure relates to a method for providing stimulation current from an implantable medical device. An embodiment of the method includes applying electrical stimulation therapy using a current output pulse generator having an adjustable compliance voltage source. The method embodiment also includes detecting a parameter dependent on tissue/electrode interface impedance. The method embodiment further includes adjusting the level of the voltage source based on the detected parameter.

This Summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

DETAILED DESCRIPTION

The following detailed description refers to the accompanying drawings which show, by way of illustration, specific aspects and embodiments in which the present invention may be practiced. These embodiments are described in sufficient detail to enable those skilled in the art to practice the invention. Other embodiments may be utilized and structural, logical, and electrical changes may be made without departing from the scope of the present invention.

The present disclosure provides a system for providing stimulation current using a current output device, or current pulse generator. Current output devices, as compared to voltage output devices, may provide superior neural recruitment characteristics during neural stimulation. However, the current output device requires a compliance voltage sufficient to drive stimulation current through a tissue/electrode interface impedance. The present disclosure provides for a variable compliance voltage that can be adjusted based on pulse amplitude and/or a detected impedance value, conserving power and thereby improving battery longevity.

System for Providing Stimulation Current

Figure 1:
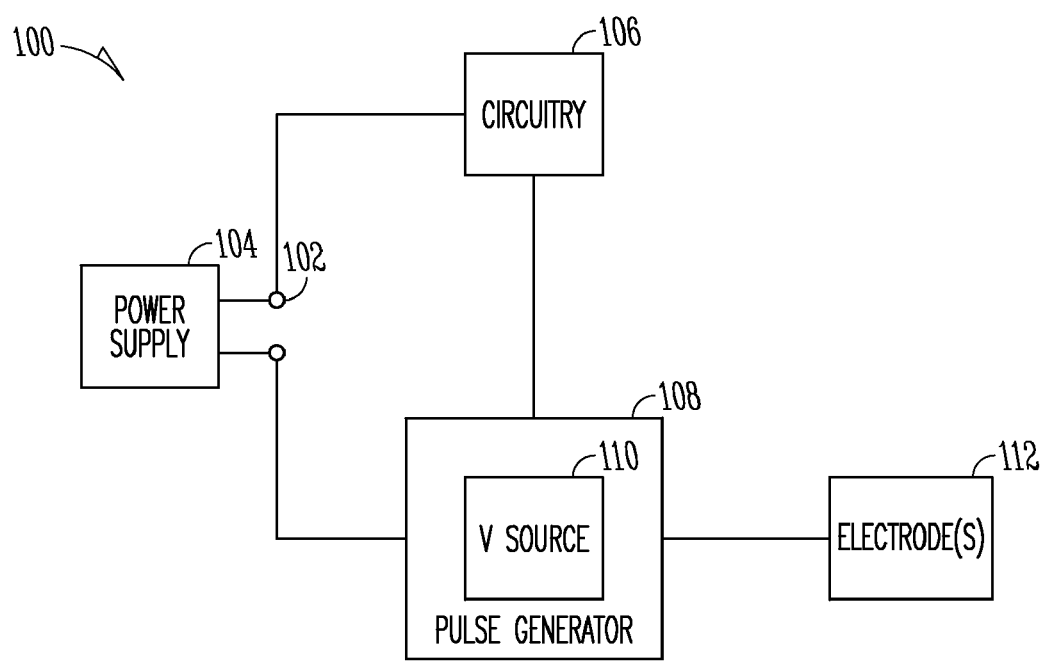
FIG. 1 illustrates a block diagram of a system for providing stimulation current, according to one embodiment.

FIG. 1 illustrates a block diagram of a system for providing stimulation current, according to one embodiment. The depicted apparatus 100 includes a power supply terminal 102 adapted to be connected to a power supply 104. The apparatus embodiment also includes circuitry 106 connected to the power supply terminal and adapted to detect a parameter dependent on impedance at an interface of at least one electrode 112 and tissue to be stimulated by the electrode (tissue/electrode interface impedance or tissue/electrode impedance). The apparatus embodiment further includes a current output pulse generator 108 adapted to deliver electrical therapy, the generator including an adjustable compliance voltage source 110 connected to the power supply terminal, the compliance voltage source having a programmable amplitude and adapted to provide different potentials for different tissue/electrode interface impedances.

Figure 5:
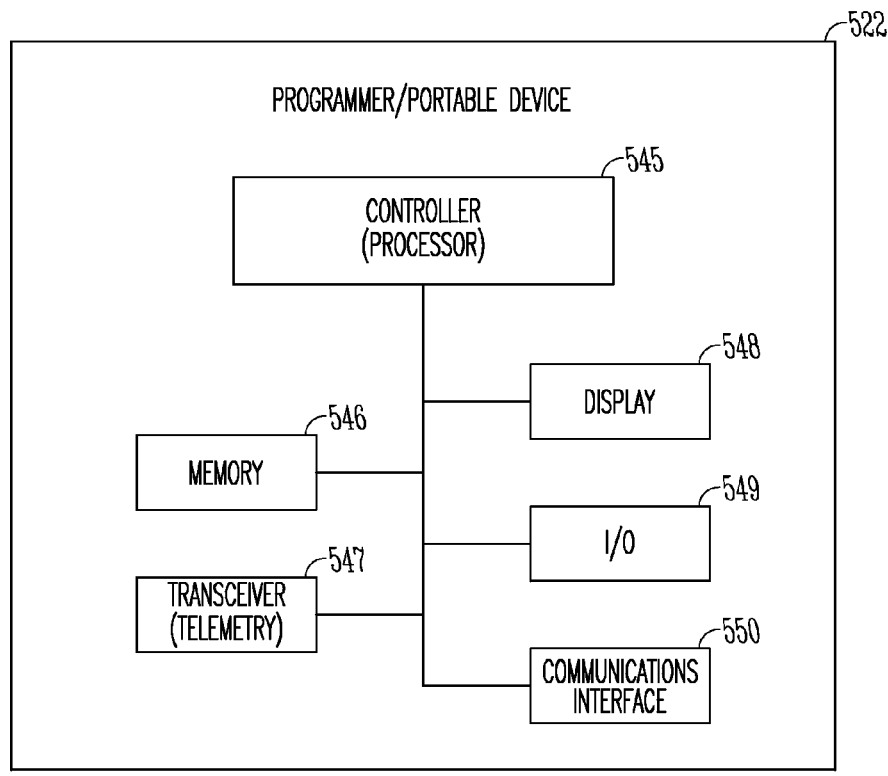
FIG. 5 illustrates a block diagram of a programmer such as illustrated in the system of FIG. 4 or other external device to communicate with the IMD(s), according to one embodiment.
Figure 6:
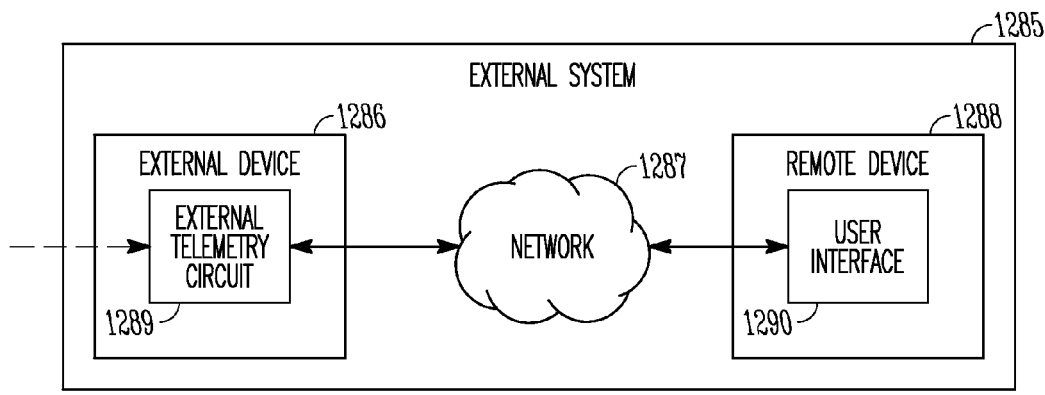
FIG. 6 is illustrates block diagram illustrating an embodiment of an external system to communicate with the IMD(s), according to one embodiment.

According to various embodiments, the voltage source 110 is adjusted using an electronic feedback loop to maintain a fixed voltage differential between the compliance voltage and a load voltage. The voltage source 110 is adjusted using a look-up table that includes a detected tissue/electrode interface impedance and a desired level of stimulation current, according to various embodiments. The voltage source can be adjusted using an external device. The external device can adjust the voltage source using a detected tissue/electrode interface impedance and a desired level of stimulation current. Examples of external devices, such as depicted in FIGS. 5 and 6, include advanced patient management systems (APM), programmers, handheld devices, and other remote devices capable of communication with an implanted apparatus.

An apparatus embodiment includes a power supply and circuitry adapted to detect tissue/electrode impedance and further adapted to be connected to the power supply. The apparatus embodiment also includes a current output pulse generator adapted to deliver electrical therapy, the generator including an adjustable compliance voltage source connected to the power supply, the compliance voltage source having a programmable amplitude and adapted to provide different potentials for different tissue/electrode interface impedances. According to various embodiments, the apparatus embodiment also includes at least one stimulating electrode, and the current output pulse generator is adapted to deliver electrical therapy using the electrode. The voltage source can be adjustable over a range from 1V to 100V and values of tissue/electrode interface impedance include a range of impedance values from 100Ω to 10 kΩ, according to various embodiments. According to various embodiments, the current output pulse generator can be adapted to deliver electrical current over a range from 5 µA to 10 mA.

Figure 3A:
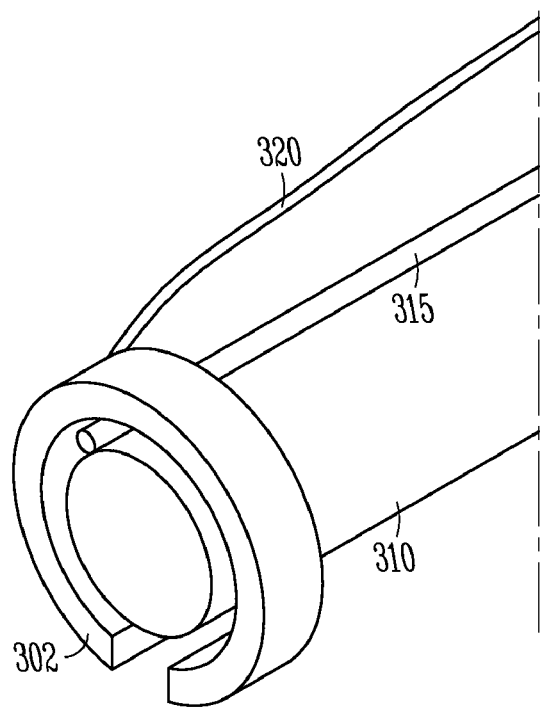
FIG. 3A illustrates a cuff electrode for use with a system for providing stimulation current, according to one embodiment.
Figure 3B:
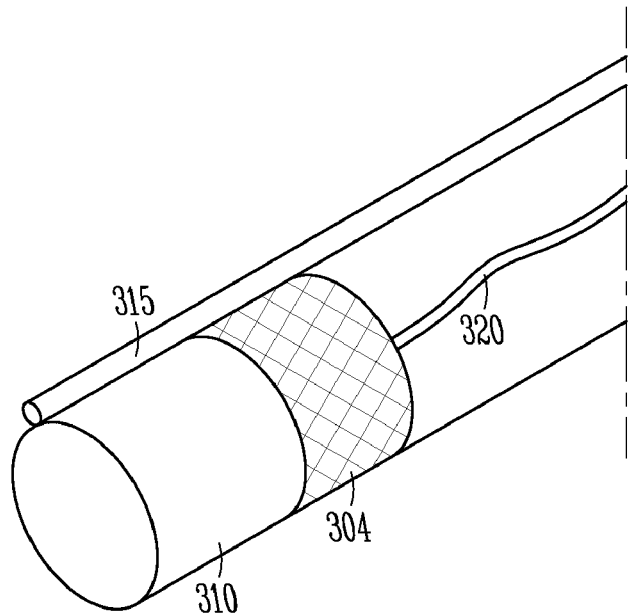
FIG. 3B illustrates a transvascular electrode for use with a system for providing stimulation current, according to one embodiment.

The apparatus can further include at least one stimulating electrode 112, wherein the current output pulse generator is adapted to deliver electrical therapy using the at least one electrode. Types of electrodes used to deliver therapy include transvascular and nerve cuff electrodes, as shown in FIGS. 3A and 3B. Other electrodes may be used without departing from the scope of this disclosure. Types of electrical therapy that can be delivered include cardiac rhythm management therapy and neural stimulation therapy such as vagal stimulation therapy. Other types of electrical therapy can be delivered by the disclosed apparatus without departing from the scope of this disclosure.

A system embodiment includes means for applying neural stimulation using a current output pulse generator having an adjustable compliance voltage source. The system embodiment also includes means for detecting a tissue/electrode interface impedance or a parameter dependent on the tissue/electrode interface impedance. The system embodiment further includes means for adjusting the level of the voltage source connected to the detecting means and the stimulating means. According to various embodiments, the applying means includes an implantable medical device. The detecting means includes a sensor and circuitry to monitor the sensor, according to various embodiments. The detecting means can include at least one electrode.

According to an embodiment, the means for adjusting the voltage source includes means for adjusting the voltage source based on a programmed amplitude of the current pulse generator. The means for adjusting the voltage source includes means for adjusting the voltage source based on detected tissue/electrode interface impedance, according to an embodiment. The means for adjusting the voltage source includes means for adjusting the voltage source based on programmed amplitude of the current source and detected tissue/electrode interface impedance, in an embodiment. According to various embodiments, the system is fully implantable. Only the stimulating means and detecting means are implantable, in an embodiment. The system further includes an enclosure, in an embodiment. The enclosure is adapted to house the stimulating means, detecting means and adjusting means in one embodiment, and is adapted to house only the stimulating means and detecting means, in another embodiment.

Figure 2:
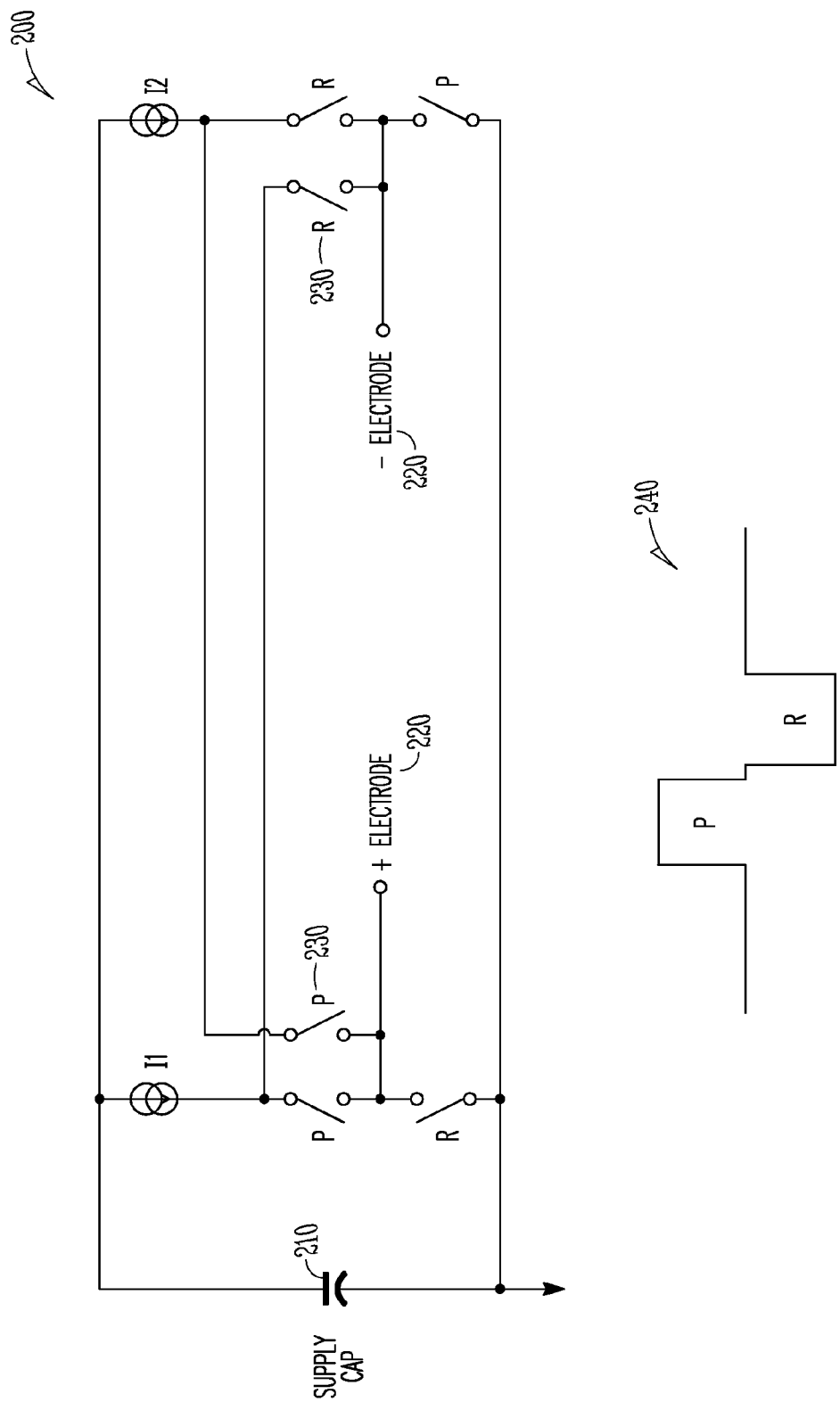
FIG. 2 illustrates a schematic diagram of a current source for providing stimulation current, according to one embodiment.

FIG. 2 illustrates a schematic diagram of a current source for providing stimulation current, according to one embodiment. The current source 200 includes a compliance voltage that includes the voltage level on supply capacitor 210. The current source 200 is used to deliver electrical therapy to electrodes 220 as shown with variable current sources I1 and I2. A number of switches 230 are used to control the delivery of electrical stimulation therapy. The switches 230 may be embodied as transistors or other switching electrical devices. The P and R designations indicate which phase is being delivered. P denotes pacing or the stimulation portion of the waveform 240 and R denotes recharge or the charge equalization portion of the waveform. The supply capacitor 210 is charged to a voltage level, the voltage level determined by multiplying the desired current by the detected impedance at the electrode/tissue interface, according to various embodiments. The impedance at the interface of the electrode and tissue can be detected or measured using a number of techniques. According to an embodiment, the electrode/tissue interface impedance is detected by forcing a known current to the electrodes and measuring the voltage at the stimulation terminals (electrodes). The electrode/tissue interface impedance is detected by applying a constant voltage to the electrodes and measuring the current through the electrodes, according to one embodiment. In an embodiment, the electrode/tissue interface impedance is detected by connecting a charged capacitor the stimulation electrodes for a pre-determined amount of time, and measuring the voltage difference across the capacitor before and after connecting it to the electrodes. The electrode/tissue interface impedance can also be detected by connecting a charged capacitor to the stimulation electrodes until the voltage difference across this capacitor achieves a predetermined value, and measuring the amount of time it takes to achieve the value, according to an embodiment.

Neural Stimulation

Neural stimulation has been the subject of a number of studies and has been proposed for several therapies. The autonomic system controls physiological activities of the body and the imbalance of autonomic tone is related to many diseases and conditions. Reduced autonomic balance (increase in sympathetic and decrease in parasympathetic cardiac tone) during heart failure has been shown to be associated with left ventricular dysfunction and increased mortality. Sympathetic inhibition, as well as parasympathetic activation, has been associated with reduced arrhythmia vulnerability following a myocardial infarction. Vagus nerve stimulation has been proposed to treat sleep disorders, gastrointestinal motility, eating disorders, obesity, anorexia, gastrointestinal tract disorders, hypertension, coma, and epilepsy. Direct electrical stimulation of parasympathetic nerves can activate the baroreflex, inducing a reduction of sympathetic nerve activity and reducing blood pressure by decreasing vascular resistance. Direct stimulation of the vagal parasympathetic fibers has been shown to reduce heart rate via the sympathetic nervous system. In addition, some research indicates that chronic stimulation of the vagus nerve may be of protective myocardial benefit following cardiac ischemic insult.

The neural stimulation can be applied to a vagus nerve, a cardiac branch of the vagus nerve, a cardiac fat pad, a baroreceptor site, or to other neural targets that stimulate the parasympathetic nervous system or inhibit the sympathetic nervous system. The neural stimulation can be applied using intravascularly-fed electrodes, nerve cuffs, satellite electrodes, and other known means for stimulating a neural target. FIG. 3A illustrates a cuff electrode for use with a system for providing stimulation current, according to one embodiment. The cuff electrode 302 is placed around nerve bundle 315 and is connected to lead 320 to apply stimulation. Nerve bundle 315 is adjacent vessel 310. FIG. 3B illustrates a transvascular (or intravascularly-fed) electrode for use with a system for providing stimulation current, according to one embodiment. The transvascular electrode 304 is placed within a vessel 310, is connected to a lead 320, and applies stimulation to an adjacent nerve bundle 315. Other electrode designs may be used without departing from the scope of this disclosure. The disclosed system and methods can be used with devices providing other types of electrical stimulation, including but not limited to pacing, defibrillation, and cardiac rhythm management therapy.

Implantable Medical Devices

Figure 4:
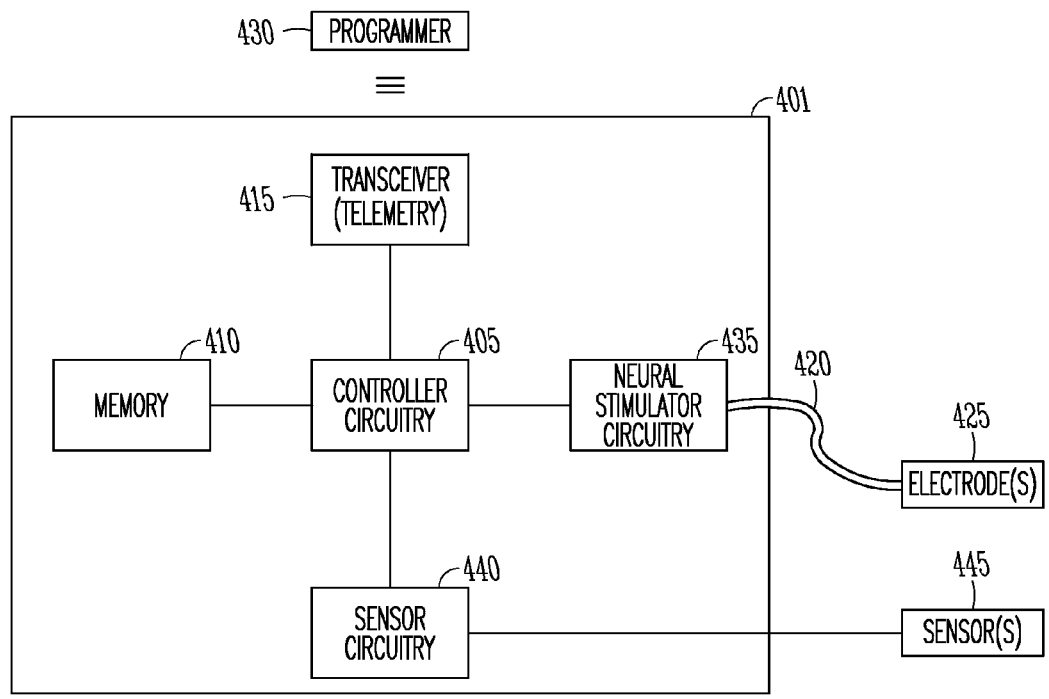
FIG. 4 illustrates a block diagram of a system with an IMD for providing stimulation current, according to one embodiment.

FIG. 4 illustrates a block diagram of a system with an IMD for providing stimulation current, according to one embodiment. The system includes an implantable medical device (IMD) 401, an electrical lead 420 coupled to the IMD 401, and at least one electrode 425. The IMD includes a controller circuit 405, a memory circuit 410, a telemetry circuit 415, and a neural stimulation circuit 435. The controller circuit 405 is operable on instructions stored in the memory circuit to deliver an electrical neural stimulation therapy. Therapy is delivered by the neural stimulation circuit 435 through the lead 420 and the electrode(s) 425. According to various embodiments, the neural stimulation circuit 435 includes a power supply, circuitry adapted to detect a parameter dependent on tissue/electrode impedance and further adapted to be connected to the power supply, a current output pulse generator adapted to deliver electrical therapy, the generator including an adjustable compliance voltage source connected to the power supply, the compliance voltage source having a programmable amplitude and adapted to provide different potentials for different tissue/electrode interface impedances, as described above in FIG. 1. The telemetry circuit 415 allows communication with an external programmer 430. The programmer 430 can be used to adjust the programmed therapy provided by the IMD 401, and the IMD can report device data (such as battery and lead resistance) and therapy data (such as sense and stimulation data) to the programmer using radio telemetry, for example. According to various embodiments, the IMD 401 applies electrical stimulation therapy using a current output pulse generator having an adjustable compliance voltage, detects tissue/electrode interface impedance, and adjusts the level of the voltage source based on the measured value of tissue/electrode interface impedance, as disclosed in the method depicted in FIG. 8, described below. The illustrated system also includes sensor circuitry 440 that is coupled to at least one sensor 445. The controller circuit 405 processes sensor data from the sensor circuitry and delivers a therapy responsive to the sensor data.

The electrical lead 420 includes a direct stimulation lead for providing stimulation directly to a nerve trunk, according to one embodiment. An example of a direct stimulation lead includes a lead with a nerve cuff, as depicted in FIG. 3A. In an embodiment, the at least one neural stimulation lead 420 includes an indirect stimulation lead for providing stimulation indirectly to a nerve trunk, through the wall of an adjacent blood vessel. Examples of indirect stimulation leads include chronically implanted transvascular neural stimulation leads, as depicted in FIG. 3B. According to various embodiments, the disclosed systems and methods can be used with a leadless device. For example, in an embodiment, one or more satellite electrodes are controlled wirelessly to deliver electrical therapy.

FIG. 5 illustrates a programmer 522, such as the programmer 430 illustrated in the system of FIG. 4 or other external device to communicate with the implantable medical device(s), according to one embodiment. An example of another external device includes Personal Digital Assistants (PDAs) or personal laptop and desktop computers in an Advanced Patient Management (APM) system. The illustrated device 522 includes controller circuitry 545 and a memory 546. The controller circuitry 545 is capable of being implemented using hardware, software, and combinations of hardware and software. For example, according to various embodiments, the controller circuitry 545 includes a processor to perform instructions embedded in the memory 546 to perform a number of functions, including communicating data and/or programming instructions to the implantable devices. The illustrated device 522 further includes a transceiver 547 and associated circuitry for use to communicate with an implantable device. Various embodiments have wireless communication capabilities. For example, various embodiments of the transceiver 547 and associated circuitry include a telemetry coil for use to wirelessly communicate with an implantable device. The illustrated device 522 further includes a display 548, input/output (I/O) devices 549 such as a keyboard or mouse/pointer, and a communications interface 550 for use to communicate with other devices, such as over a communication network.

FIG. 6 is illustrates block diagram illustrating an embodiment of an external system to communicate with the IMD(s), according to one embodiment. The external system 1285 includes a programmer, in some embodiments. In the embodiment illustrated in FIG. 6, the external system includes a patient management system. As illustrated, external system 1285 is a patient management system including an external device 1286, a telecommunication network 1287, and a remote device 1288. External device 1286 is placed within the vicinity of an IMD and includes external telemetry system 1289 to communicate with the IMD. Remote device(s) 1288 is in one or more remote locations and communicates with external device 1286 through network 1287, thus allowing a physician or other caregiver to monitor and treat a patient from a distant location and/or allowing access to various treatment resources from the one or more remote locations. The illustrated remote device 1288 includes a user interface 1290.

Methods for Making a System for Providing Stimulation

Figure 7:
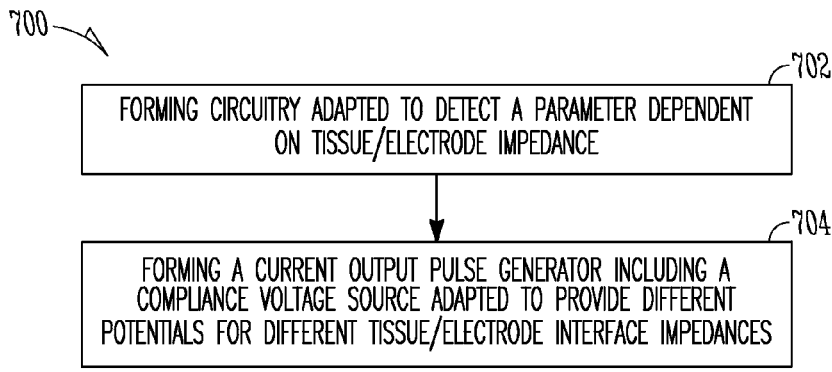
FIG. 7 illustrates a flow diagram of a method for making a system for providing stimulation current from an IMD, according to one embodiment.

FIG. 7 illustrates a flow diagram of a method for making a system for providing stimulation current from an IMD, according to one embodiment. An embodiment of the method 700 includes forming circuitry adapted to detect a parameter dependent on tissue/electrode impedance, at 702. The method embodiment also includes forming a current output pulse generator adapted to deliver electrical therapy, the generator including a compliance voltage source having a programmable amplitude and adapted to provide different potentials for different tissue/electrode interface impedances, at 704.

According to various embodiments, forming a current output pulse generator includes forming the voltage source to be adjusted using an electronic feedback loop to maintain a fixed voltage differential between the compliance voltage and a load voltage. Forming a current output pulse generator includes the forming the voltage source to be adjusted using a look-up table that includes a measured tissue/electrode interface impedance and a desired level of stimulation current, according to various embodiments. Forming a current output pulse generator includes the forming the voltage source to be adjusted using an external device, in an embodiment. The external device, such as a programmer (FIG. 5) or patient management system (FIG. 6) adjusts the voltage source using a measured tissue/electrode interface impedance and a desired level of stimulation current, in various embodiments.

Methods for Providing Stimulation Current

Figure 8:
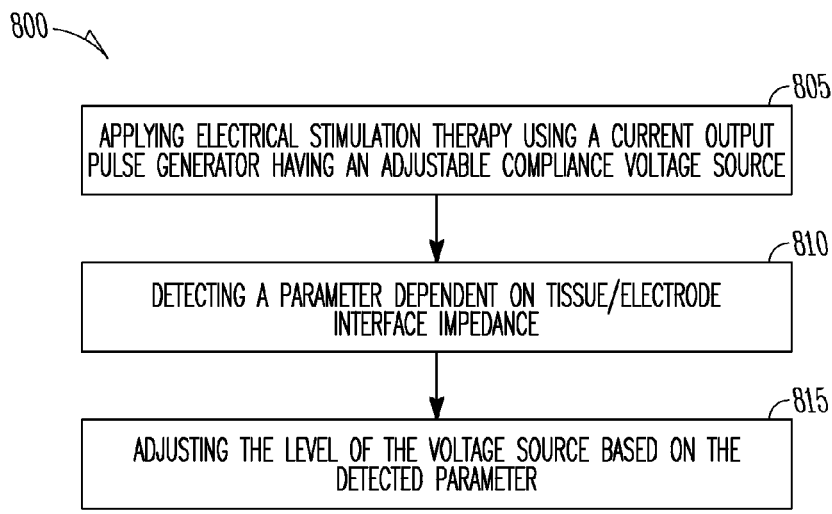
FIG. 8 illustrates a flow diagram of a method for providing stimulation current from an implantable medical device, according to one embodiment.

FIG. 8 illustrates a flow diagram of a method for providing stimulation current from an implantable medical device, according to one embodiment. An embodiment of the method 800 includes applying electrical stimulation therapy using a current output pulse generator having an adjustable compliance voltage source, at 805. The method embodiment also includes detecting a parameter dependent on tissue/electrode interface impedance, at 810. The method embodiment further includes adjusting the level of the voltage source based on the detected parameter, at 815. According to various embodiments, applying electrical stimulation therapy includes applying neural stimulation therapy, such as vagal stimulation therapy. The method further includes adjusting the voltage source based on a programmed amplitude of the current pulse generator, according to an embodiment.

One of ordinary skill in the art will understand that, the modules and other circuitry shown and described herein can be implemented using software, hardware, and combinations of software and hardware. As such, the illustrated modules and circuitry are intended to encompass software implementations, hardware implementations, and software and hardware implementations.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. An apparatus for delivering electrical neural stimulation therapy to a patient, the apparatus comprising:
   a power supply;
   circuitry connected to the power supply and adapted to detect tissue/electrode interface impedances;
   at least one stimulating electrode, wherein the circuitry includes a charged capacitor adapted to be electrically connected to the at least one stimulating electrode; and
   a current output pulse generator connected to the at least one stimulating electrode, the generator comprising a programmed amplitude of stimulation current, wherein the generator is configured to deliver electrical neural stimulation therapy at the programmed amplitude, the generator further comprising:
   an adjustable compliance voltage source connected to the power supply, the voltage source configured to provide an adjustable voltage level and different potentials for the different tissue/electrode interface impedances, the voltage source comprising:
   a supply capacitor;
   two variable current sources connected in parallel with the supply capacitor; and
   switches configured to control the delivery of electrical neural stimulation therapy, wherein the switches are connected to the current sources and supply capacitor, wherein the pulse generator is configured to receive the detected impedances, maintain the programmed amplitude of stimulation current for the different tissue/electrode interface impedances and adjust the compliance voltage source by adjusting the voltage level based on the programmed amplitude of the stimulation current and the detected impedances; and
   wherein the charged capacitor is adapted to be electrically connected to the at least one stimulating electrode for a pre-determined amount of time, and wherein the tissue/electrode interface impedances are determined by measuring a voltage difference across the charged capacitor before and after connecting it to the at least one electrode.

2. The apparatus of claim 1, wherein the voltage source is adjustable over a range from 1V to 100V.

3. The apparatus of claim 1, wherein the circuitry is configured to detect tissue/electrode interface impedances in a range of impedance values from 100Ω to 2 kΩ.

4. The apparatus of claim 1, wherein the current output pulse generator is configured to deliver electrical current over a range from 5 µA to 10 mA.

5. The apparatus of claim 1, wherein the apparatus is fully implantable.

6. The apparatus of claim 1, wherein the apparatus is partially implantable, and current output pulse generator of the apparatus is implantable.

7. The apparatus of claim 1, further comprising an enclosure configured to house the power supply, the current output pulse generator, the adjustable compliance voltage source and the circuitry.

8. The apparatus of claim 1, further comprising an enclosure configured to house the current output pulse generator and the circuitry.

9. The apparatus of claim 1, further comprising an electronic feedback loop, wherein the apparatus is configured to adjust the voltage source using the electronic feedback loop to maintain a fixed voltage differential between the compliance voltage level and a load voltage.

10. The apparatus of claim 1, wherein the apparatus is configured to communicate with an external device to adjust the compliance voltage source.

11. The apparatus of claim 10, wherein the external device is part of an advanced patient management system (APM).

12. The apparatus of claim 1, further comprising a controller adapted to receive the detected impedances, maintain the programmed amplitude of stimulation current for the different tissue/electrode interface impedances.

13. The apparatus of claim 1, further comprising a telemetry circuit.

14. An apparatus for delivering electrical neural stimulation therapy to a patient, the apparatus comprising:
   a power supply;
   circuitry connected to the power supply and adapted to detect tissue/electrode interface impedances;
   at least one stimulating electrode, wherein the circuitry includes a charged capacitor adapted to be electrically connected to the at least one stimulating electrode; and
   a current output pulse generator connected to the at least one stimulating electrode, the generator comprising a programmed amplitude of stimulation current, wherein the generator is configured to deliver electrical neural stimulation therapy at the programmed amplitude, the generator further comprising:
   an adjustable compliance voltage source connected to the power supply, the voltage source configured to provide an adjustable voltage level and different potentials for the different tissue/electrode interface impedances, the voltage source comprising:
   a supply capacitor;
   two variable current sources connected in parallel with the supply capacitor; and
   switches configured to control the delivery of electrical neural stimulation therapy, wherein the switches are connected to the current sources and supply capacitor, wherein the pulse generator is configured to receive the detected impedances, maintain the programmed amplitude of stimulation current for the different tissue/electrode interface impedances and adjust the compliance voltage source by adjusting the voltage level based on the programmed amplitude of the stimulation current and the detected impedances; and
   wherein the charged capacitor is adapted to be connected to the stimulating electrodes until a voltage difference across the charged capacitor achieves a predetermined value, and wherein the tissue/electrode interface impedances are determined by measuring an amount of time to reach the predetermined value.

15. The apparatus of claim 14, wherein the neural stimulation therapy includes vagal stimulation therapy.

16. The apparatus of claim 14, wherein the at least one stimulating electrode includes a transvascular electrode.

17. The apparatus of claim 14, wherein the at least one stimulating electrode includes nerve cuff electrode.

18. The apparatus of claim 14, wherein the apparatus is connected to a memory with a look-up table stored therein, wherein the look-up table includes tissue/electrode interface impedance and desired level of stimulation current, wherein the apparatus is configured to adjust the voltage source using the look-up table the circuitry includes a charged capacitor adapted to be electrically connected to the stimulating electrodes.

* * * * *